(12) United States Patent
Neeser et al.

(10) Patent No.: US 6,592,906 B2
(45) Date of Patent: Jul. 15, 2003

(54) ANTICARIOGENIC DAIRY PRODUCT AND ITS USE

(75) Inventors: Jean-Richard Neeser, Savigny (SZ); Bernhard Guggenheim, Erlenbach (SZ); Claude Parmantier, Glos (FR)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/776,647

(22) Filed: Feb. 5, 2001

(65) Prior Publication Data

US 2001/0033887 A1 Oct. 25, 2001

Related U.S. Application Data

(63) Continuation of application No. PCT/EP99/05335, filed on Jul. 20, 1999.

(30) Foreign Application Priority Data

Aug. 7, 1998 (EP) ............................................. 98202658

(51) Int. Cl.[7] .............................................. A61K 35/20
(52) U.S. Cl. ....................... 424/535; 424/520; 424/550; 424/551; 424/94.1
(58) Field of Search ................................. 424/520, 535, 424/550, 551, 94.1

(56) References Cited

U.S. PATENT DOCUMENTS

| 2,376,693 A | 5/1945 | Helmer et al. ................. 99/54 |
| 2,928,742 A | 3/1960 | Kennedy et al. ............... 99/56 |
| 4,992,420 A | 2/1991 | Neeser ........................... 514/8 |
| 4,994,441 A | 2/1991 | Neeser ........................... 514/8 |
| 5,015,628 A | 5/1991 | Reynolds ...................... 514/12 |
| 5,368,869 A | 11/1994 | Savello et al. ................ 426/42 |
| 5,427,769 A | 6/1995 | Berrocal et al. .............. 424/54 |
| 5,503,865 A | 4/1996 | Behringer et al. .......... 426/587 |
| 5,532,022 A | * | 7/1996 | Miller et al. |
| 5,639,502 A | 6/1997 | Behringer et al. .......... 426/587 |
| 5,833,953 A | 11/1998 | Berrocal et al. .............. 424/49 |

FOREIGN PATENT DOCUMENTS

| EP | 0 117 321 A2 | 9/1984 |
| GB | 1123647 | 5/1998 |
| JP | 51 079762 | 7/1976 |

OTHER PUBLICATIONS

Pridmore et al., "Variacin, a new lanthionine–containing bacteriocin produced by Micrococcus varians: comparison to lacticin 481 of *Lactococcus lactis*", Appl Environ Microbiol, May 1996: 62(5):1799–802, abstract.*

Abstract XP–002090244 Harper et al., "Cariostatic Evaluation of Cheeses with Diverse Physical and Compositional Characteristics", Caries Research,, vol. 20, No. pp. 123–130 (1986).

Abstract XP–002090245 Hansen et al., "Stabilization of rennet treated skim milk by carrageenan", Journal of Diary Science, vol. 63, p. 50 (1980).

Abstract XP–002090246 M. M. Omar, "Size distribution of casein micelles during mild coagulation", Food Science Dep., vol. 29, No. 2, pp. 119–124 (1985).

B. Pause et al., "Comparative examination of anti–caries effect of cheeses",(Results and Conclusions) Milchwissenschaft, vol. 48, No. 3 p/ 137–141 (1993).

B. Pause et al., "Comparative examination of anti–caries effect of cheeses", (Materials and Methods) Milchwissenschaft, vol. 47 No. 11 pp. 697–700 (1992).

Clinical Nutrition, "Cheese and Dental Caries", Nutrition /Reviews, vol. 46, No. 6, pp. 215–217 (1988).

* cited by examiner

Primary Examiner—Leon B. Lankford, Jr.
Assistant Examiner—Ruth Davis
(74) Attorney, Agent, or Firm—Winston & Strawn

(57) ABSTRACT

The invention relates to a food composition containing an effective quantity of rennetted milk for preventing or treating dental caries or dental plaque. The invention also relates to a method of preparing the composition.

16 Claims, No Drawings

ANTICARIOGENIC DAIRY PRODUCT AND ITS USE

CROSS-REFERENCE TO RELATED APPLICATIONS

This application is a continuation of the U.S. national stage designation of International Application No. PCT/EP99/05335, filed Jul. 20, 1999, the content of which is expressly incorporated herein by reference thereto.

FIELD OF THE INVENTION

The present invention relates to a dairy product possessing anticariogenic properties as well as food compositions prepared from the product.

BACKGROUND OF THE INVENTION

Some products derived from milk are of great interest for dentiboccal health. Thus, anticariogenic properties are recognized for casein in certain forms and for some of its derivatives. A few cheeses, for example, are known for their anti-caries activity (Nutrition Reviews, 46, 215–217, 1988; Pause, B. and Lembke, J., Milchwissenschaft, 47, 697–700, 1992; Pause, B. and Lernbke, J., Milchwisssenschaft, 48, 137–141, 1993).

U.S. Pat. No. 5,427,769 to Berrocal et al. describes a method for preventing the appearance of dental caries by placing in contact with the teeth a food composition containing micellar casein in a sufficient quantity to inhibit colonization by *Streptococcus sobrinus*, the principal bacterial agent involved in carious pathology. U.S. Pat. No. 5,833,953 to Berrocal et al. also describes the use of fluorinated micellar caseins or their micellar subunits for treating plaque or dental caries.

U.S. Pat. No. 4,992,420 to Neeser describes the treatment of the buccal cavity with κ-caseinoglycomacropeptides (CGMP) derived from whey in order to eradicate dental plaque and caries. Likewise, U.S. Pat. No. 4,994,441 to Neeser describes an anti-plaque and anti-caries composition in which the active agent is chosen from κ-caseinoglycopeptides.

Furthermore, U.S. Pat. No. 5,015,628 to Reynolds describes an anticariogenic composition containing, as an active agent, particular phosphopeptides obtained, for example, by trypsin hydrolysis of α- and β-caseins.

All of these patents describe processes that do not belong to the technology of fresh dairy products. The processes currently used to manufacture such fresh products lead to acidic products, such as yogurt, fromage frais or "petit suisse". In such products, acid coagulation of casein leads to its decalcification, thus bringing about the loss of some of its anticariogenic properties. Likewise, the CGMP contained in these products is not hydrolyzed, and as a result is not in an active form.

The present invention is intended to overcome these disadvantages, by providing a fresh dairy product having optimized anticariogenic properties.

SUMMARY OF THE INVENTION

The invention relates to an anticariogenic food composition that includes an effective quantity of rennetted milk for preventing or treating dental caries or dental plaque. In one embodiment, the composition includes at least 10% by weight rennetted milk.

In another embodiment, the rennetted milk in the composition comprises both caseinoglycomacropeptide (CGMP) in hydrolyzed form and coagulated casein complexed with calcium, these compounds being in their active form, wherein the CGMP enhances the anti-caries and anti-plaque activity of the food composition. In a preferred embodiment, the rennetted milk includes at least 0.05% by weight CGMP and at least 2% by weight complexed casein.

The composition may further include a sweetener, such as xylitol, aspartame, sucrose, tagatose, or a maltose/fructose mixture. The composition may further be provided in powdered form and may further include a flavoring or coloring.

The invention also relates to a method for preparing a food composition for preventing or treating dental caries or dental plaque, including providing whole milk or milk enriched with fat, adding powdered milk to form a milk mixture, adding water to the milk mixture to form a paste, adding to the paste, a solution including 10% agar/gelatin to form a gel, filtering the gel to form a filtered mixture, pasteurizing the filtered mixture to form a pasteurized mixture, heating the pasteurized mixture, homogenizing the pasteurized mixture to form a homogenized mixture, adding to the homogenized mixture, calcium chloride and rennet to form a rennetted mixture, and curdling the rennetted mixture.

In one embodiment, potassium sulfate is added to the milk mixture. In a preferred embodiment, the whole milk or milk enriched with fat has a fat content greater than 4%. The rennet is preferably added in a $1/15000$ solution. In the preferred embodiment, the rennetted mixture includes 0.02% to 0.05% by weight calcium chloride and 0.005% to 0.008% by weight rennet. In another embodiment, the pasteurized mixture is homogenized for less than 30 minutes.

DETAILED DESCRIPTION OF THE INVENTION

In this description, all percentages are indicated by weight relative to the total weight, unless otherwise stated.

The rennetted milk according to the present invention is used to prepare food compositions intended for preventing or treating dental caries or dental plaque. The milk contains caseinoglycomacropeptide (CGMP) in free, hydrolyzed form, and coagulated casein complexed with calcium (calcified casein).

CGMP is a glycopeptide hydrolyzed from kappa-casein by the action of rennet. CGMP is present in the coagulation whey and is not separated during the process for the preparation of the rennetted milk. The quantity of free CGMP present in the rennetted milk is preferably between 0.05 and 0.2%, which represents 1.5 to 6% of the protein matter.

Calcified casein is also produced by the action of the rennet on the casein. The casein has lost its micellar form as happens for other fresh dairy products such as yogurts or acidic cheeses. Unlike the latter, however, the casein retains some of the properties of the micelle and remains in a calcified form. The calcified casein content of the rennetted milk is preferably greater than 2%.

The rennetted milk according to the invention is also rich in calcium. This calcium is present in two forms, one which is associated with casein, and the other which is free. The minimum concentration of calcium contained in the rennetted milk is 1.75 g/L.

The rennetted milk according to the invention has the characteristic of grouping together these two anti-caries compounds, CGMP and calcified casein in their active forms. Tests carried out in vivo show that it has anticariogenic properties superior to those of other dairy products such as, for example, yogurt. This surprising result is explained by a synergistic effect between CGMP in hydrolyzed form and calcified casein.

It is possible to prepare a mixture containing at least 80% milk, in the form of whole milk or milk enriched with fat, and 1 to 10% powdered milk, so as to increase the dry matter content. It is possible to add potassium sorbate in an amount of about 0.1% by weight, so as to protect the product from molds.

The whole milk or milk enriched with fat may be used in liquid or powdered form. The fat content is preferably greater than 4%. The milk preferably has a dry matter content of at least 8%.

Water is added to the mixture to form a paste. The paste can then be gelled by adding a solution containing 10% agar/gelatin, at a temperature of 50° C. The addition is made by dispersion at cold temperature. The gelatin may be replaced with a gum for example.

The mixture may be filtered before being pasteurized at 125° C. for about 20 seconds. The mixture can then be heated to 70° C. before being homogenized at a pressure of about 200 bars. Next, after preliminary cooling of the mixture to around 45° C., calcium chloride ($CaCl_2$) in a 30 to 33% solution and rennet in a 1/15000 solution are added, for example. The $CaCl_2$ is preferably between 0.02 and 0.05% by weight relative to the mixture. The rennet may be used in a 1/15000 solution of 0.005 to 0.008%. The mixture is then stirred. The conditions are such that the milk-based mixture does not curdle during this rennetting step. To keep the mixture from curdling, the duration of homogenization of the mixture at around 45° C. is preferably less than 30 minutes.

The mixture may then be packaged at, for example, a temperature of 43° C., and may then be kept in an oven at 43° C. for 1 to 2 hours for curdling. A rennetted milk is obtained, which coagulated at neutral pH and which still contains, at the end of the process, a quantity of free CGMP and casein complexed with calcium.

This process thus makes it possible to group together and to preserve, in a simple manner, these two anticariogenic and anti-dental plaque constituents in their active forms—the casein in a calcified form and the CGMP in a hydrolyzed form.

The rennetted milk is used in the preparation of various food compositions, such as for example, gelled milk, with storage lives of 2, 3, or 4 weeks. Powdered compositions may also be prepared, as the fresh product may be, for example, spray-dried so as to obtain it in a powdered form.

These compositions contain an effective quantity of the rennetted milk with an optimized anti-caries and anti-plaque activity. To treat dental caries, the minimum effective quantity of rennetted milk is preferably greater than 10%. It is possible to enhance the anti-caries activity of such compositions by adding, for example, CGMP.

The compositions may be sweetened by the addition of 1 to 5% of a sweetener, preferably xylitol. Aspartame, sucrose, tagatose or a maltitol/fructose mixture may also be used as sweeteners. The compositions may also be flavored.

EXAMPLES

Tests were carried out to compare the anticariogenic effect of the rennetted milk with that of some other fresh dairy products such as, for example, yogurt (Example 1). The results on the in vivo effects have shown a significantly greater efficacy of rennetted milk in anticariogenic activity.

The examples described below are not limiting and serve merely to illustrate the invention. The percentages and parts are indicated by weight unless otherwise stated.

Example 1

Rennetted Milk

A paste was prepared by mixing 86 kg of milk enriched with 5% fat and having a dry matter content of 8% with 7.3 kg of powdered milk at 1% and then 120 g of potassium sorbate. The paste was gelled by adding 400 g of a 10% agar/gelatin solution (200° B). The addition was carried out at a temperature of 50° C. and by dispersion at cold temperature. The mixture was then filtered before being pasteurized at 125° C. for 20 seconds. It was then heated to 70° C. and homogenized at a pressure of 200 bars. The mixture was allowed to cool to a temperature of 45° C. to 46° C. It was then supplemented with 50 g of 30 to 33% calcium chloride ($CaCl_2$) solution and 8 g of 1/15000 rennet solution. The mixture was stirred for less than 30 minutes at 45° C.

The mixture was then kept in an oven at 43° C. for 1 to 2 hours. A rennetted milk was obtained, coagulated at neutral pH and which contained about 0.1% free CGMP and about 2% casein complexed with calcium. This rennetted milk was used as a base in the preparation of various anticariogenic food compositions.

Example 2

Comparison of the Effects of the Rennetted Milk and of Plain Yogurt on Caries in Rats Three compositions were prepared which contain no sucrose: a rennetted milk corresponding to the invention, prepared according to Example 1; a traditional plain yogurt; and a control based on soya bean protein (flour) (control $D_0$). Three identical compositions were made with the addition of 10% sucrose, the last being the control $D_1$.

The anti-caries effect of the rennetted milk obtained according to the invention was compared with that of the traditional yogurt, both products containing or not containing 10% sucrose.

Six groups of ten rats were infected orally twice a day by inoculating them with suspensions of *Streptococcus sobrinus* and *Actinornyces viscosus*. To promote the implantation of these bacteria, the rats were given sweetened water containing 3% of glucose and 3% of sugar for several days. These rats were then fed according to a precise program divided into six distinct treatments described in Table 1. All the rats followed a "highly cariogenic" basic regime ($D_2$), distributed in the form of 18 daily rations. The rats were provided alternately with 18 "highly cariogenic" rations and 18 rations, either fresh dairy products described above in treatments 3, 4, 5, and 6, or controls $D_0$ and $D_1$ in control treatments 1 and 2 respectively. The effects of the treatments on the progression of the dental plaque, on the incidence of caries, and on the oral flora in the rats were then studied.

A control group of rats followed treatment 1 based on soya bean protein. The results for this group served as references for treatments 3 and 4. A second control group of rats which followed treatment 2 (soya bean protein+10% sucrose) served as control for treatments 5 and 6.

TABLE 1

Number of rations distributed for the treatments and controls 1 to 6.

| | | Treatments | | | | | |
|---|---|---|---|---|---|---|---|
| | Diets | 1 (control) | 3 | 4 | 2 (control) | 5 | 6 |
| Number of Rations | 0.4 g $D_2$ basic diet | X18 | X18 | X18 | X18 | X18 | X18 |
| | 0.4 g $D_1$ control with sugar | | | | X18 | | |
| | 0.4 g $D_0$ control without sugar | X18 | | | | | |
| | 1 g of rennetted milk | | X18 | | | | |
| | 1 g of yogurt | | | X18 | | | |
| | 1 g of rennetted milk + 10% sugar | | | | | X18 | |
| | 1 g yogurt + 10% sugar | | | | | | X18 |

TABLE 2

Compositions of the basic diet $D_2$ controls $D_1$ and $D_0$ given according to Table 1.

| Diets Ingredients | $D_2$ "highly cariogenic" | $D_1$ "slightly cariogenic" | $D_0$ "non cariogenic" |
|---|---|---|---|
| Caster sugar | 56% | 10% | — |
| Skimmed milk "substitute" based on soya bean flour* | 28% | 28% | 28% |
| Wheat flour | 8% | 54% | 64% |
| Beer yeast | 5% | 5% | 5% |
| Gevral protein | 2% | 2% | 2% |
| Sodium chloride | 1% | 1% | 1% |

*43.8% soya bean extract, 54.9% lactose, 0.8% $CaCl_2 \cdot 2H_2O$, 0.4% L-Met and 0.1% L-Lys.

The initial (T) and advanced (B) dental fissures, as well as the caries on the smooth surfaces (E) were analyzed. The results are shown in Table 3.

TABLE 3

Mean values per rat of the initial dental fissures (T), advanced dental fissures (B) and caries on the smooth surfaces (E).

| Treatments | TΔΔ | BΔΔ | EΔΔΔ |
|---|---|---|---|
| 1 (control without sugar) | 11.5 | 9.2 | 17.5 |
| 3 rennetted milk | 10.3 | 6.1 | 5.4 |
| 4 yogurt | 11.3 | 7.3 | 8.3 |
| 2 (control with sugar) | 11.8 | 9.9 | 16.9 |
| 5 sweetened rennetted milk | 11.9 | 10.3 | 10.9 |
| 6 sweetened yogurt | 11.7 | 9.9 | 10.8 |

ΔΔ = 12 fissures maximum,
ΔΔΔ = 20 units of caries maximum.

The results showed that among the 2 unsweetened fresh dairy products, only the rennetted milk corresponding to the invention caused a significant reduction in the T lesions (treatment 3 vs. 1). Yogurt did not significantly affect the development of these lesions. When these products were sweetened (treatments 5, 6 vs. 2), they had no effect on these same lesions.

The results of the tests also showed that rennetted milk had a clear and significant action on the reduction of the B lesions, whereas the action of yogurt was statistically at the limit of what was significant (treatments 3, 4 vs. 1). The sweetened dairy products (treatments 5, 6 vs. 1) had no effect on these lesions.

As regards the action on caries on the smooth surfaces (E), the action of the 2 fresh dairy products was very significant, that of rennetted milk being substantially greater (treatment 3 vs. 1). These same products when sweetened (treatments 5, 6 vs. 2) had an effect which was still significant.

The unsweetened rennetted milk reduced all types of caries more substantially than when it was sweetened (treatment 3 vs. 5). Table 4 shows a summary of the results.

TABLE 4

Comparative percentages of reduction of caries (B) and (E).

| | Advanced dental fissures (B) | Caries on the smooth surfaces (E) |
|---|---|---|
| Control without sugar | 9.2 caries = 100% | 17.5 caries = 100% |
| Plain yogurt | 21% fewer caries | 53% fewer caries |
| Rennetted milk | 34% fewer caries | 69% fewer caries |

The results showed that these two fresh products had a clear anti-caries activity. The rennetted milk according to the invention which contains CGMP in a free hydrolyzed form and calcified casein, however, showed a substantially higher anti-caries activity. This effect was even more pronounced against caries on the smooth surfaces.

Example 3
Infant Formula Having Anticariogenic Properties

A composition for a fresh milk was prepared by mixing:

| | |
|---|---|
| Rennetted milk prepared according to Example 1 | 10.0% |
| Demineralized whey powder containing 12.5% protein | 64.9% |
| Milk fat | 20.6% |
| Maize oil | 4.4% |
| $K_2HPO_4$ | 0.1% |

Example 4
Anticariogenic Composition for Baby Food

The following were mixed:

| | |
|---|---|
| Rennetted milk prepared according to Example 1 | 12.6% |
| Demineralized whey powder containing 12.5% protein | 22.9% |
| Lactose | 34.9% |
| Milk fat | 20.4% |
| Maize oil | 4.6% |
| Minerals, micronutrients and water | 4.6% |

Example 5
Milk Drink Composition

A composition for a milk drink is prepared by mixing:

| | |
|---|---|
| Rennetted milk prepared according to Example 1 | 10–15 g |
| Lactose | 5–10 g |
| Water | 70–90 g |

These components yield a 100 gram mixture.

Example 6

The rennetted milk prepared according to Example 1 was supplemented with 1 to 2% of variacin in bacteriocin powder form as described in European Patent No. 0,759,469. The refrigerated composition obtained had the anticariogenic properties of rennetted milk and an extended storage life.

Example 7

A sweetened and flavored refrigerated food composition was prepared from the rennetted milk obtained in Example 2. 5 g of xylitol and 2 g of flavoring agent were added to 100 g of rennetted milk obtained according to Example 2. The composition obtained was a fresh dairy product having a nice sweet taste and an optimized anticariogenic activity.

Example 8
Refrigerated Food Composition

A sweetened and flavored refrigerated food composition was prepared from the following ingredients:

| | |
|---|---|
| Skimmed milk | 78–82% |
| Cream containing 40% fat | 10–12% |
| Skimmed milk powder | 6–8% |
| Agar/gelatin | 0.4–2% |
| Potassium sorbate | 0.05–0.2% |
| Aspartame/acesulfame | 0.02–0.06% |
| Flavorings/colorings (strawberry, banana and the like) | 0.05–0.2% |
| Total | 100% |

The mixture was heated to 70° C. and then homogenized at a pressure of 200 bars. The mixture was pasteurized at 110° C. for 6 minutes and then cooled to 43° C. The mixture was rennetted with about 4 g of rennet 1/15000 per 100 kg of mixture. The product was packaged and then coagulated for about 1 hour 30 minutes and then cooled to 4° C.

A variation of the composition was prepared using, as source of sugar, about 7.5% of the following mixture: 1:4 to 4:1 of maltitol and 4:1 to 1:4 of fructose. In order not to exceed 100%, the quantity of skimmed milk was reduced.

The composition obtained is a fresh dairy product having a nice sweet taste and an optimized anticariogenic and anti-plaque activity containing a minimum of 0.05% CGMP in an active form and a minimum of 2% complexed casein.

Example 9

A stirred rennetted milk was prepared from the mixture described in Example 8, but after cooling to 4° C., about 10% fromage frais or yogurt (so as not to exceed 100%, the quantity of skimmed milk was reduced) was added and then the mixture was stirred, made smooth, and packaged. A stirred, flavored, fresh dairy product was obtained having an anti-caries and anti-plaque activity.

Example 10
Refrigerated Food Composition

A refrigerated food composition having an optimized anti-caries and anti-plaque activity was prepared from the following ingredients:

| | |
|---|---|
| Skimmed milk | 30–35% |
| Cream containing 40% fat | 27% |
| Skimmed milk powder | 3–5% |
| Starch | 2–4% |
| Maltitol/fructose | 15–18% |
| Cocoa powder | 2% |
| Fromage frais | 10% |

Trisodium citrate and flavorings were added and then the mixture was brought to 100% by adding water.

The milk-cream-milk powder mixture was heated at 110° C. for about 2 minutes and then cooled to 43° C. The mixture was rennetted with about 4 g of mixture for 1 hour and 30 minutes and then heated to 85° C. and the other ingredients were added. The mixture was homogenized under pressure and treated at 130° C. for about 40 seconds and packaged after cooling.

Example 11
Powdered Anti-Caries Composition

Milk (skimmed where appropriate) was pasteurized and then cooled to between 10° C. and 40° C. before about 0.1% rennet was added and then allowed to act for 60 to 600 minutes. The mixture was homogenized under pressure and then the fats were added. The mixture was heated to 70° C., homogenized again and then heated to 120° C. The mixture was concentrated by about 50% and dried (spray-drying) after homogenization.

The powdered composition thus obtained had the same anti-caries and anti-plaque properties as the fresh dairy products according to the invention. The quantities of CGMP and casein in their active forms were as described above in the description.

What is claimed is:

1. An anticariogenic mixture comprising a food composition that includes an effective quantity of rennetted milk for preventing or treating dental caries or dental plaque, wherein the rennetted milk comprises at least 0.05% by weight caseinoglycomacropeptide (CGMP) in hydrolyzed form and at least 2% by weight coagulated casein complexed with calcium, the CGMP and complexed casein being in the active form, wherein the active forms of CGMP and casein enhance the anti-caries and anti-plaque activity of the food composition.

2. The anticariogenic mixture of claim 1 comprising at least 10% by weight rennetted milk.

3. The anticariogenic mixture of claim 1, further comprising a sweetener.

4. The anticariogenic mixture of claim 3, wherein the sweetener is xylitol, aspartame, sucrose, tagatose, or a maltose/fructose mixture.

5. The antic ariogenic mixture of claim 1, provided in powdered, gelled, or liquid form.

6. The anticariogenic mixture of claim 1, further comprising a flavoring or coloring.

7. The anticariogenic mixture of claim 1, wherein the CGMP is between 0.05% and 0.2%.

8. The anticariogenic mixture of claim 1, further comprising demineralized whey containing 12.5% protein, maize oil, or lactose.

9. The anticariogenic mixture of claim 1, wherein the rennetted milk comprises at least 1.75 g/l of calcium.

10. The anticariogenic mixture of claim 1, wherein the composition is in the form of an infant formula or baby food having anticariogenic activity.

11. The anticariogenic mixture of claim 10, further comprising demineralized whey, milk fat, and maize oil.

12. The anticariogenic mixture of claim 1, further comprising $K_2HPO_4$, agar, gelatin, or lactose.

13. The anticariogenic mixture of claim 1, wherein the composition is in the form of a milk drink having anticariogenic activity, wherein, the milk drink further comprises lactose and water.

14. The anticariogenic mixture of claim 1, further comprises 1 to 2% variacin.

15. An anticariogenic food composition that includes an effective quantity of rennetted milk for preventing or treating dental caries or dental plaque, wherein the rennetted milk comprises between 0.05% and 0.2% by weight caseinoglycomacropeptide (CGMP) in hydrolyzed form, at least 2% by weight coagulated casein complexed with calcium, and at least 1.75 g/l of calcium, wherein the CGMP and complexed casein are in the active form, and the active forms of CGMP and casein enhance the anti-caries and anti-plaque activity of the food composition.

16. A powdered anti-caries composition which includes an effective quantity of powered rennetted milk for preventing or treating dental caries or dental plaque, wherein the rennetted milk comprises at least 0.05% by weight caseinoglycomacropeptide (CGMP) in hydrolyzed form, at least 2% by weight coagulated casein complexed with calcium, and at least 1.75 g/l of calcium, wherein the CGMP and complexed casein are in the active form, and the active forms of CGMP and casein enhance the anti-caries and anti-plaque activity of the powdered anti-caries composition.

* * * * *

UNITED STATES PATENT AND TRADEMARK OFFICE
CERTIFICATE OF CORRECTION

PATENT NO.      : 6,592,906 B2
DATED           : July 15, 2003
INVENTOR(S)     : Neeser et al.

It is certified that error appears in the above-identified patent and that said Letters Patent is hereby corrected as shown below:

<u>Title page,</u>
Item [75], Inventors, after "Jean-Richard Neeser, Savigny", delete "(SZ)" and insert -- (CH) --; and after "Bernhard Guggenheim, Erlenbach", delete "(SZ)" and insert -- (CH) --.

<u>Column 8,</u>
Line 57, delete "antic ariogenic" and insert -- anticariogenic --.

Signed and Sealed this

Fourteenth Day of October, 2003

JAMES E. ROGAN
*Director of the United States Patent and Trademark Office*